(12) United States Patent
Yazicioglu et al.

(10) Patent No.: US 12,403,316 B2
(45) Date of Patent: Sep. 2, 2025

(54) NEURAL INTERFACE DEVICE FOR STIMULATION OF A NERVE AND MEASURING IMPEDANCE

(71) Applicant: Galvani Bioelectronics Limited, Brentford (GB)

(72) Inventors: Refet Firat Yazicioglu, Brentford (GB); Rizwan Bashirullah, Brentford (GB); Gerald Edwin Hunsberger, Jr., Brentford (GB)

(73) Assignee: GALVANI BIOELECTRONICS LIMITED, Stevenage (GB)

( * ) Notice: Subject to any disclaimer, the term of this patent is extended or adjusted under 35 U.S.C. 154(b) by 0 days.

(21) Appl. No.: 16/619,392

(22) PCT Filed: Dec. 20, 2018

(86) PCT No.: PCT/GB2018/053728
§ 371 (c)(1),
(2) Date: Dec. 4, 2019

(87) PCT Pub. No.: WO2019/122905
PCT Pub. Date: Jun. 27, 2019

(65) Prior Publication Data
US 2020/0306534 A1    Oct. 1, 2020

Related U.S. Application Data

(60) Provisional application No. 62/608,438, filed on Dec. 20, 2017.

(51) Int. Cl.
*A61N 1/36* (2006.01)
*A61N 1/05* (2006.01)

(52) U.S. Cl.
CPC ......... *A61N 1/3614* (2017.08); *A61N 1/0556* (2013.01); *A61N 1/36175* (2013.01)

(58) Field of Classification Search
CPC . A61N 1/3614; A61N 1/0556; A61N 1/36175
See application file for complete search history.

(56) References Cited

U.S. PATENT DOCUMENTS 5,919,220 A * 7/1999 Stieglitz ............... A61N 1/0556
607/118
6,406,421 B1 * 6/2002 Grandjean .......... A61M 60/882
600/17

(Continued)

FOREIGN PATENT DOCUMENTS

CN        104220129 A    12/2014
JP      2013000404 A      1/2013

(Continued)

OTHER PUBLICATIONS

International Search Report and Written Opinion, International Application No. PCT/GB2018/053728, mailing date Mar. 21, 2019, 17 pages.

(Continued)

*Primary Examiner* — Jon Eric C Morales
(74) *Attorney, Agent, or Firm* — Merchant & Gould P.C.

(57) ABSTRACT

A system for stimulation of a nerve and measuring impedance. The system includes a neural interface device including a plurality of electrodes; a voltage or current source operatively connected to at least a subset of the electrodes, wherein the voltage or current source is configured to generate an electrical signal to be applied to the electrodes; an impedance measuring module operatively connected to at least a subset of the electrodes, wherein the impedance measurement module is configured to measure the impedance between the electrodes; and a controller arranged to determine an amplitude of an action potential induced in the nerve, via the electrical signal, based on the measured (Continued)

impedance and to adjust the electrical signal in order to induce an action potential having a target amplitude.

24 Claims, 7 Drawing Sheets

(56) References Cited

U.S. PATENT DOCUMENTS

| | | | |
|---|---|---|---|
| 2003/0050677 A1* | 3/2003 | Gross | A61N 1/36071 607/72 |
| 2006/0224187 A1* | 10/2006 | Bradley | A61N 1/37241 607/2 |
| 2007/0208394 A1* | 9/2007 | King | A61N 1/36139 607/62 |
| 2008/0177338 A1 | 7/2008 | Ben-David et al. | |
| 2009/0024189 A1* | 1/2009 | Lee | A61N 1/37247 607/66 |
| 2011/0040547 A1* | 2/2011 | Gerber | G16H 20/17 703/11 |
| 2011/0087085 A1* | 4/2011 | Tsampazis | A61N 1/36039 600/379 |
| 2012/0136411 A1 | 5/2012 | Bradley | |
| 2013/0073008 A1* | 3/2013 | Ternes | A61N 1/36157 607/62 |
| 2013/0150940 A1* | 6/2013 | Wilson | A61B 5/4094 607/118 |
| 2015/0066108 A1* | 3/2015 | Shi | A61N 1/36139 607/59 |
| 2015/0202433 A1* | 7/2015 | Franke | A61N 1/0556 607/72 |
| 2015/0360031 A1* | 12/2015 | Bornzin | A61N 1/36139 607/62 |
| 2016/0220823 A1* | 8/2016 | Ranu | A61N 1/0553 |
| 2016/0250476 A1* | 9/2016 | Kaemmerer | A61N 1/36185 607/45 |
| 2016/0310741 A1* | 10/2016 | Baru | A61N 1/36185 |
| 2016/0346534 A1* | 12/2016 | Isaacson | A61N 1/36185 |
| 2017/0197077 A1* | 7/2017 | Harpak | A61B 5/6843 |
| 2017/0239470 A1* | 8/2017 | Wei | A61N 1/36164 |
| 2018/0071530 A1* | 3/2018 | Giftakis | A61N 1/36142 |
| 2018/0185651 A1* | 7/2018 | Astrom | A61N 1/3614 |
| 2021/0136411 A1 | 5/2021 | Zhang et al. | |

FOREIGN PATENT DOCUMENTS

| | | |
|---|---|---|
| WO | WO2015/168162 A1 | 11/2015 |
| WO | 2016137796 A1 | 9/2016 |

OTHER PUBLICATIONS

International Preliminary Report on Patentability, International Application No. PCT/GB2018/053728, mailing date Jul. 2, 2020, 12 pages.
Japanese Office Action received for Japanese Application No. 2020-533775 mailed on Jan. 10, 2023, 12 pgs.
Chinese Search Report, dated Mar. 8, 2024, Application No. CN201880081853.9.

* cited by examiner

NEURAL INTERFACE DEVICE FOR STIMULATION OF A NERVE AND MEASURING IMPEDANCE

PRIORITY CLAIM

The present application is a National Phase entry of PCT Application No. PCT/GB2018/053728, filed Dec. 20, 2018, which claims priority from U.S. Provisional Application No. 62/608,438, filed Dec. 20, 2017, each of which is hereby fully incorporated herein by reference.

TECHNICAL FIELD

This disclosure relates to a neural interface device, a system, a method, a computer program and a computer-readable medium for stimulation of a nerve and measuring impedance.

BACKGROUND

Typically, devices for stimulating nerves (i.e. neuromodulation devices) require means to ensure that stimulation is delivered at the correct level. For instance, it may be necessary to ensure that stimulation is delivered to the nerve at a particular amplitude, or for a particular duration. In other words, it may be necessary to ensure that the correct "dose" of stimulation is delivered to the nerve.

In order to monitor the dose of stimulation provided to a nerve by a neuromodulation device, some form of feedback is required. However, direct feedback is not available for rheumatoid arthritis (RA) therapies. This is because immune system modulation and associated effects on RA symptoms are only visible within hours, days or months after stimulation, rather than being observable immediately. Cytokine analysis does not provide fast (or real-time) feedback regarding the actuation of the nerve.

Therefore, there exists a need to estimate the amount of neural actuation or stimulation induced in a nerve. In addition, there exists a need to ensure that the charge delivered to a nerve associated with splenic artery induces a sufficient level of action potential that will yield therapy.

SUMMARY

In one aspect, there is a system for stimulation of a nerve and measuring impedance, the system comprising: a neural interface device comprising a plurality of electrodes for electrically contacting the nerve; a voltage or current source operatively connected to at least a subset of the electrodes, wherein the voltage or current source is configured to generate an electrical signal (also referred to as a stimulating electrical signal) to be applied to the electrodes; an impedance measuring module operatively connected to at least a subset of the electrodes, wherein the impedance measurement module is configured to measure the impedance between the electrodes; and a controller arranged to determine an amplitude of an action potential induced in the nerve or a quantified indication of a change in downstream effect caused by an action potential induced in the nerve, via the electrical signal, based on the measured impedance and to adjust the electrical signal in order to induce an action potential having a target amplitude or a targeted change in downstream effect caused by the action potential. The action potential may refer to a compound action potential evoked by a pulse or train of pulses (the electrical signal).

In other words, there is a system for stimulation of a nerve and monitoring stimulation dose response based on impedance, the system comprising: a neural interface device comprising a plurality of electrodes for electrically contacting the nerve; a voltage or current source operatively connected to at least a subset of the electrodes, wherein the voltage or current source is configured to generate an electrical signal to be applied to the electrodes; an impedance measuring module operatively connected to at least a subset of the electrodes, wherein the impedance measurement module is configured to measure impedance between the electrodes; and a controller arranged to determine a dose response induced by the electrical signal based on the measured impedance and to adjust the electrical signal in order to induce a target dose response.

In another aspect, there is a neural interface device for stimulation of a nerve and measuring impedance, the device comprising: a pair of stimulation electrodes for inducing an electrical signal in the nerve; a pair of impedance measurement electrodes for measuring impedance between the impedance measurement electrodes; wherein the pair of stimulation electrodes are spaced apart from one another in a longitudinal direction with respect to the nerve; wherein the pair of impedance measurement electrodes are spaced apart from one another in a direction perpendicular to the longitudinal direction with respect to the nerve.

In another aspect, there is a system for stimulation of a nerve and measuring impedance, the system comprising: one or more neural interface devices described herein; and a voltage or current source operatively connected to each pair of stimulation electrodes of each neural interface device described herein, wherein the voltage or current source is configured to generate an electrical signal to be applied to the nerve via the stimulation electrodes; and an impedance measurement module operatively connected to each pair of impedance measuring electrodes, wherein the impedance measurement module is configured to measure the impedance between the pair of impedance measuring electrodes.

In another aspect, there is a method for stimulation of a nerve and measuring the impedance, the method comprising: providing one or more neural interface devices described herein; generating an electrical signal to be applied to the nerve via the stimulation electrodes of the neural interface device by at least one voltage or current source operatively connected to the stimulation electrodes; and measuring the impedance between the impedance measuring electrodes of the neural interface device by at least one impedance measuring module operatively connected to the impedance measuring electrodes.

In another aspect, there is a computer program comprising code portions which, when loaded and run on a computing device, cause the computing device to: generate an electrical signal to be applied to a nerve via the stimulation electrodes of the neural interface device described herein by at least one voltage or current source operatively connected to the stimulation electrodes; and measure the impedance between the impedance measuring electrodes of the neural interface device described herein by at least one impedance measuring module operatively connected to the impedance measuring electrodes.

In some embodiments, in relation to the aspects discussed above, the controller may be arranged to adjust the electrical signal based on the measured impedance without determining an amplitude of an action potential induced in the nerve. Instead, an expected (predetermined) indication of correlation between the impedance and downstream effect of the compound action potential or dose response is determined by the controller instead. For example, the controller may have access to a table of data including correlation data between a measured impedance (or indication of impedance) value and a dose response (which may include various physiological responses) and based on this correlation data, the controller may determine the expected impedance value for the target dose response. Based on this, the stimulating electrical signal may be adjusted to meet the target dose response. Various other correlation data which may be predetermined (or/and in some cases this correlation data may be collected during use or installation of the system) for use in a similar manner. In other examples, other established relationship definitions (e.g. a function) may be used in addition to or in place of use of a table to determine the correlation and thus adjust the electrical signal based on the measured impedance. These are mere examples and other methods of using relationship between different elements may be used to determine change in the stimulation signal to reach a target dose response, a target amplitude or downstream effect of the electrical signal applied.

In other words, impedance is used to infer the recruitment of compound action potential caused by the stimulating electrical signal. The downstream effect is correlated to the compound action potential activity. Thus, impedance is used to infer the downstream effect correlated to the compound action potential activity. Such inferred downstream effect may be quantified and stimulating electrical signal may be adjusted based on the relative change in the quantified indicated downstream effect in order to induce an action potential having a desired (or target) downstream effect or target dose-response.

Thus, the controller does not necessarily determine an amplitude of an action potential induced, but instead determines an indication of a downstream effect caused by the action potential thereof (such as splenic arterial flow, mean arterial blood pressure, heart rate, for example). In view of the correlation between the downstream effect and the impedance measured, the electrical signal can also be adjusted in order to induce the desired downstream effect.

In other words, an electrical dose-response system is provided for monitoring dose response and adjusting the electrical signal to meet a target dose response, which may include inducing an action potential having a target amplitude or downstream effect caused by the action potential having a target amplitude.

A measurement of an electrical dose-response may comprise a response to a sequence of electrical pulses (e.g. a stimulating electrical signal) of increasing charge applied in a fixed intermitted manner consisting of ON and OFF phases, wherein the ON phase may comprise of a fixed number of stimulation pulses at a fixed stimulation frequency, wherein the OFF phase may consist of no stimulation pulses for a fixed duration or a sequence of subthreshold pulses known not to cause a physiological response which allows the neurovascular bundle to return to a baseline.

The impedance measuring module may be configured to measures a relative change in impedance in response to an applied dose of electrical signal comprising a sequence of stimulation pulses, wherein the relative change of impedance is a change in impedance with respect to a baseline impedance before the application of the electrical signal.

Thus, the impedance measuring module may measure the real-time change in impedance due to an applied dose comprising of a sequence of stimulation pulses.

The relative change in impedance with respect to baseline may represent a measure of the response caused by local activation of the nerve fascicle resultant from the applied dose, where such local nerve activation is an indirect measure of desired target engagement for neuromodulation therapy.

The impedance measurement which is a representative measure of the response to an applied dose is at least proportionally correlated to such dose. Thus, there may be provided a means to quantify the relative response to any applied dose of fixed amplitude to produce a full dose-response curve by increasing the dose amplitude and measuring the resulting change in impedance in real-time for each dose.

The full dose-response may comprise the response to a sequence of electrical pulses of increasing charge applied in a fixed intermitted manner consisting of ON and OFF phases, wherein the ON phase may comprise of a fixed number of stimulation pulses at a fixed stimulation frequency, wherein the OFF phase may consist of no stimulation pulses for a fixed duration or a sequence of subthreshold pulses known not to cause a physiological response which allows the target to return to baseline.

An access resistance and polarization capacitance, which are components that an impedance comprises, may be measured directly from the differential voltage induced across the stimulation electrodes.

The electrode-tissue interface access resistance may be extracted from the voltage at the rising (or leading) edge of the stimulation pulse.

The polarization capacitance of the electrode-tissue interface may be extracted from difference between the peak electrode voltage at the falling (or lagging) edge and the rising edge of the stimulation pulse.

The access resistance is strongly correlated with local activation of the neurovascular bundle under the electrodes.

The impedance may also be extracted from the differential voltage measured across the stimulating electrodes while applying a subthreshold sequence of pulses in between two dosing pulses Thus, real-time change in impedance measured across the plurality of stimulating electrodes may be used to assess a dose response.

The impedance change may be measured by extracting real-time change in access resistance and/or polarization capacitance directly from compliance voltage across the plurality of stimulating electrodes during the stimulation pulse.

The impedance change may be measured by detecting the impedance of a subthreshold signal injected between stimulation pulses across the plurality of stimulating electrodes.

A dose response may be determined from real-time change in impedance, wherein the changes in impedance are correlated to changes in arterial blood flow changes during an applied dose, wherein the changes in impedance are correlated to changes in blood pressure during the applied dose, wherein the changes in impedance are correlated to changes in heart-rate during the applied dose, and wherein changes in impedance are correlated to changes in respiratory rate during the applied dose.

A dose response determined using impedance response measurements may be correlated to changes in blood flow, blood pressure, heart rate, respiratory rate, or other physiological variable, wherein the correlation is deterministic and repeatable to assess an effectiveness of electrical neuromodulation, wherein the measurements are used to titrate therapy over time, wherein the measurements are used as a diagnostic chronic tool, and wherein the measurements are used to assess an intraoperative effectiveness of electrical neuromodulation.

Although some of the above aspects refer to stimulation electrodes and impedance measuring electrodes, a single pair of electrodes may be configured to function as both stimulation electrode and impedance measuring electrodes. In other words, it is not essential for two separate pairs of electrodes to be used such that each pair is used for stimulation and impedance measuring respectively. In other words, a single pair of electrodes may be configured to function as both the pair of stimulation electrodes and the pair of impedance measurement electrodes.

Measuring impedance as referred to throughout this specification includes directly and indirectly measuring impedance. For example, measuring impedance may include measuring an impedance indicative parameter and/or a component of impedance, such as voltage and/or current. Various examples are provided throughout this specification.

Thus, according to some aspects, a number of different methods of measuring (or evaluating) impedance have been discussed above. In one method, the impedance is evaluated by voltage build-up at the electrode during the stimulation period (TPW) and dividing it with the current amplitude ($I_{STIMp}$). In another method, impedance is measured by injecting a subthreshold current in between stimulation pulses, where the impedance is evaluated by measuring voltage generated over the electrodes and dividing it by subthreshold current amplitude. The subthreshold waveforms could be sinusoidal waves or could be square wave pulses at an amplitude that is lower than an amplitude needed to induce nerve activation. In yet another method, impedance is measured by simply measuring the polarization capacitance ($\Delta V_C$) or the access resistance ($\Delta V_R$) of the impedance change induced by a stimulation pulse and/or a subthreshold stimulation.

Measuring impedance using the subthreshold signal as described in above various embodiments enables impedance measurement regardless of stimulation status without evoking any physiological response in a subject. In other words, using a subthreshold signal enables a dose response monitoring without evoking any physiological response in a subject. Thus, a constant and/or an uninterrupted impedance measurement or dose response monitoring can be carried out.

A subthreshold frequency does not evoke any action potential. A frequency of such subthreshold frequency may be between 100 Hz-5 kHz, and an amplitude of such subthreshold frequency may be between 10 μA-6 mA or 10 μA-2 mA, for example (but these ranges may vary depending on the sensitivity of the system/electrodes).

BRIEF DESCRIPTION OF THE DRAWINGS

Embodiments of the invention will be described, by way of example, with reference to the following drawings, in which.

DETAILED DESCRIPTION

The present disclosure involves applying an electrical signal to, and thereby modulating the neural activity of, a nerve (for instance a nerve supplying the spleen) wherein the nerve is associated with a neurovascular bundle. The nerve may be a splenic arterial nerve.

Other embodiments involve applying an electrical signal to at least one of splenic arterial nerve and the splenic artery. In other embodiments, the invention may involve applying an electrical signal to all splenic arterial nerves and the splenic artery.

The neural interface device disclosed herein includes a pair of stimulation electrodes and a separate pair of impedance measurement electrodes. The stimulation electrodes are positioned longitudinally with respect to one another in order to induce differential voltage along the nerve and hence to induce actuation of the nerve. As noted in the summary section, in some examples the stimulation electrodes and impedance measurement electrodes are not provided as separate pairs of electrodes. Thus, in some examples, the same pair of electrodes may function as both stimulation and impedance measurement electrodes.

In one embodiment, the impedance measurement electrodes are positioned perpendicular to the longitudinal direction of the nerve. This ensures that the stimulation potential appears as a common mode signal in measurements made between the pair of impedance measuring electrodes.

Figure 1:
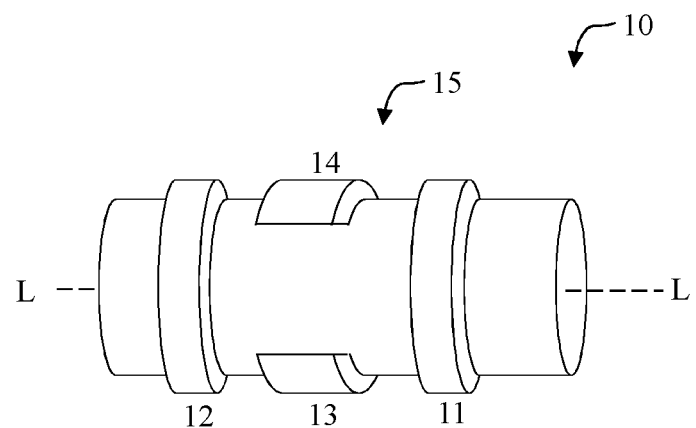
FIG. 1 illustrates a neural interface device.
Figure 4:
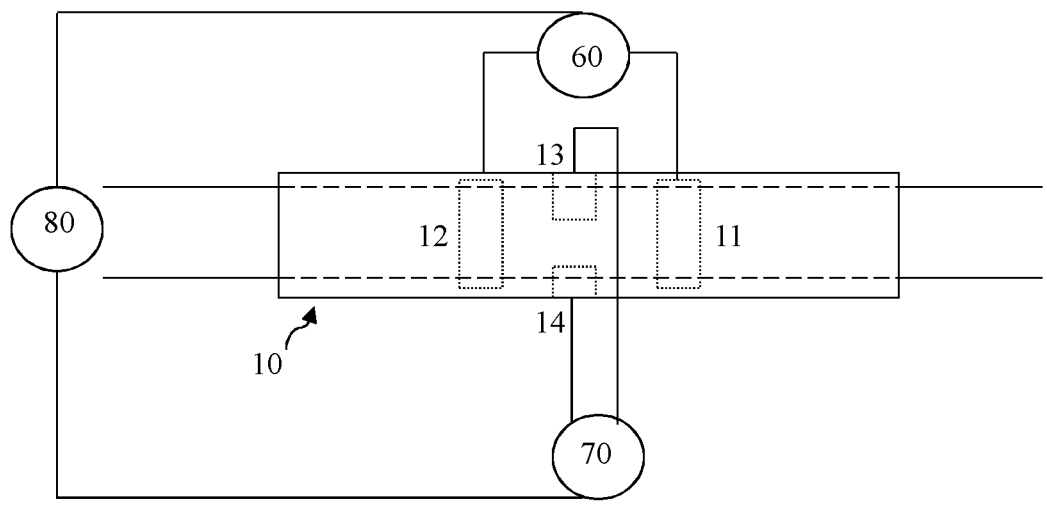
FIG. 4 illustrates a neural stimulation and impedance measuring system.

With reference to FIGS. 1 and 4, the neural interface device 10 comprises an electrode arrangement 15. The electrode arrangement 15 is configured to be placed on or around the nerve when the neural interface device 10 is in use. The electrode arrangement 15 includes a pair of stimulation electrodes 11, 12 which are spaced apart from each other so as to define a first gap between each of the stimulation electrodes 11, 12, where the first gap is positioned along the longitudinal axis L-L of the nerve (i.e. in the direction of the longitudinal axis of the nerve). In addition, the electrode arrangement 15 of FIG. 1 includes a pair of impedance measuring electrodes 13, 14 separated by a second gap between each of the impedance measuring electrodes 13, 14. The second gap is positioned along an axis which is perpendicular to the longitudinal axis L-L of the nerve. In this example, the impedance measuring electrodes 13, 14 are positioned in between the stimulation electrodes 11, 12. However, in an alternative embodiment the pair of impedance measuring electrodes 13, 14 could be placed at a position distal or proximal to both electrodes in the pair of stimulation electrodes 11, 12. In a further example, the impedance measuring electrodes 13, 14 are positioned outside the stimulation electrodes 11, 12, in other words not between stimulation electrodes 11, 12. In one embodiment impedance electrode 13 is positioned outside of stimulation electrode 11 and impedance electrode 14 is positioned outside of stimulation electrode 12. Impedance measuring electrodes 13 and 14 may partially circumvent the nerve or may fully circumvent the nerve. In the embodiments where the impedance measuring electrodes 13 and 14 fully circumvent the nerve, the second gap is positioned along an axis parallel to the longitudinal axis L-L of the nerve.

A neural interface device 10 according to the disclosure is a device that is in physical contact with a nerve. When an electrical signal is applied to the nerve via the neural interface device 10, the neural interface device 10 causes stimulation of neural activity in the nerve, for instance in a human or an animal subject.

The first electrode 11 and the second electrode 12 are preferably cuff type electrodes (for example, spiral cuff, helical cuff or flat interface) which at least partially circumvent the nerve. For example, the first electrode 11 and the second electrode 12 shown in FIG. 1 are flat interface cuff electrodes which fully circumvent the nerve. However, other types of electrodes known in the art are also suitable for use in the electrode arrangement 15. For instances, one or more of flat interface electrodes, mesh electrodes, linear rod-shaped lead electrodes, paddle-style lead electrodes, disc contact electrodes, hook electrodes, sling electrodes, intrafascicular electrode, intravascular electrode, glass suction electrodes, paddle electrodes, and percutaneous cylindrical electrodes may be used.

The first electrode 11 and second electrode 12 may fabricated from, or be partially or entirely coated with, a high charge capacity material such as platinum black, iridium oxide, titanium nitride, tantalum, poly(elthylenedioxythiophene), poly(3,4-ethylenedioxythiophene):p-toluenesulfonate (PEDOT:PTS or PEDT) and suitable combinations thereof, such as platinum-iridium alloy.

Figure 3A:
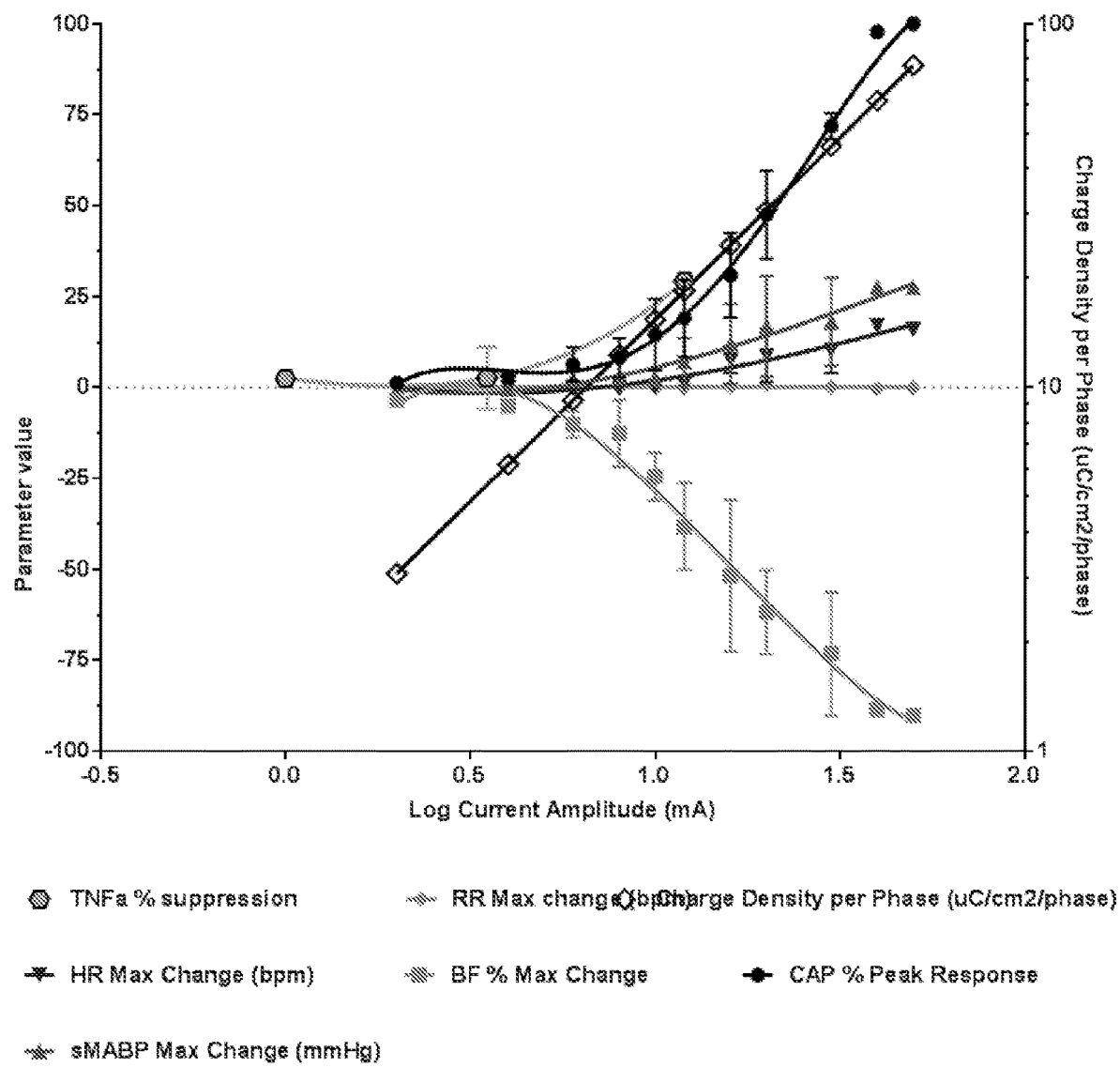
FIG. 3A illustrates a graph illustrating that blood flow in the splenic artery is correlated with the evoked compound action potential (eCAP) in a nerve.

Referring to FIG. 3A, it has been established from in-vivo experiments that the blood flow in the splenic artery is correlated with evoked compound action potentials (eCAPs). The device, systems and method described herein present a technique for measuring blood flow or vasoconstriction during stimulation and using this as a surrogate marker for induced action potentials. This biomarker can be used to ensure that a correct level of action potential is induced in the nerve and to ensure that efficacious therapy is delivered to the patient.

Figure 3B:
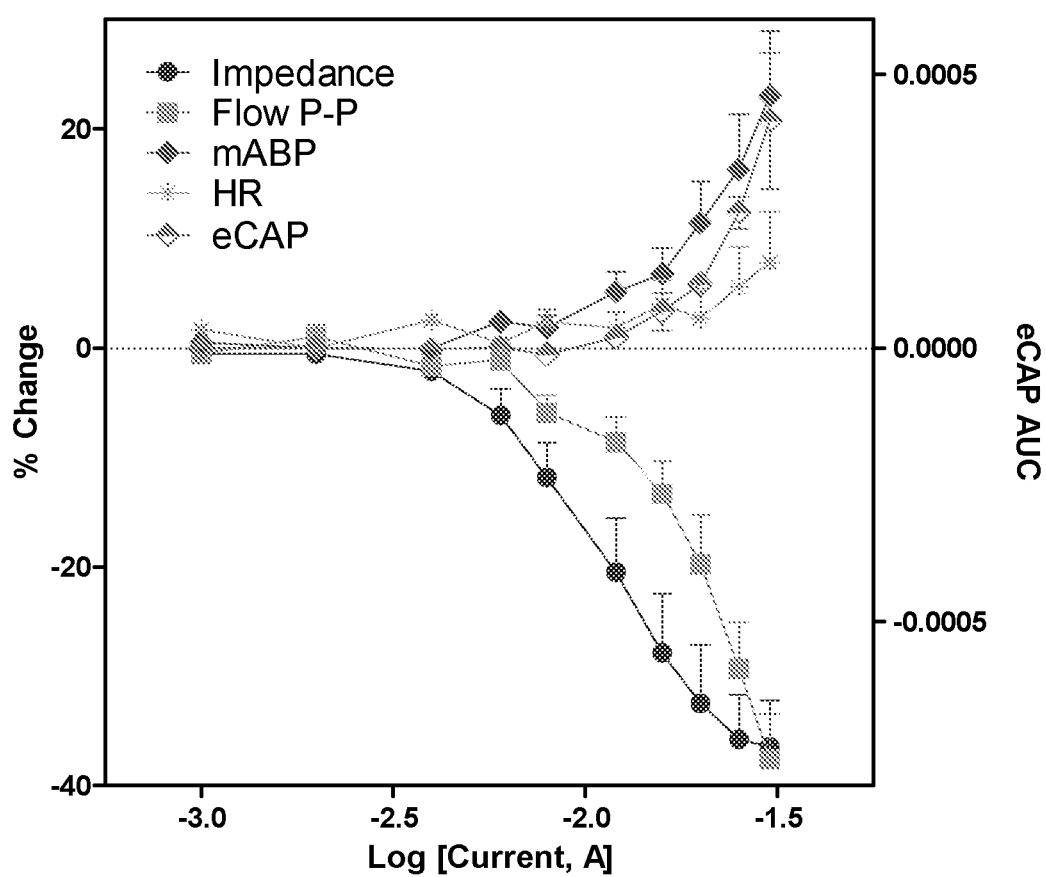
FIG. 3B illustrates a graph showing the effect of porcine splenic plexus stimulation on impedance, Rinf (circles), splenic arterial flow (squares), mean arterial blood pressure (diamonds), heart rate (asterisk), and eCAP (half-filled diamonds) following 0.4 ms biphasic stimulation at 10 Hz for 1 min.

FIG. 3B illustrates a graph showing the effect of porcine splenic plexus stimulation on impedance (access resistance), splenic arterial flow, mean arterial blood pressure, heart rate and eCAP. Impedance was calculated from the rising phase of the voltage trace from each stimulation pulse. Change in impedance (access resistance) for given stimulation was calculated in reference to the baseline resistance prior to the 1 mA stimulation. It can be seen from FIG. 3B that the measured impedance provides a dose dependent response similar to other biomarkers of splenic nerve activation including blood flow, mean arterial blood pressure, heart rate and eCAP within the splenic nerve.

Figure 3C:
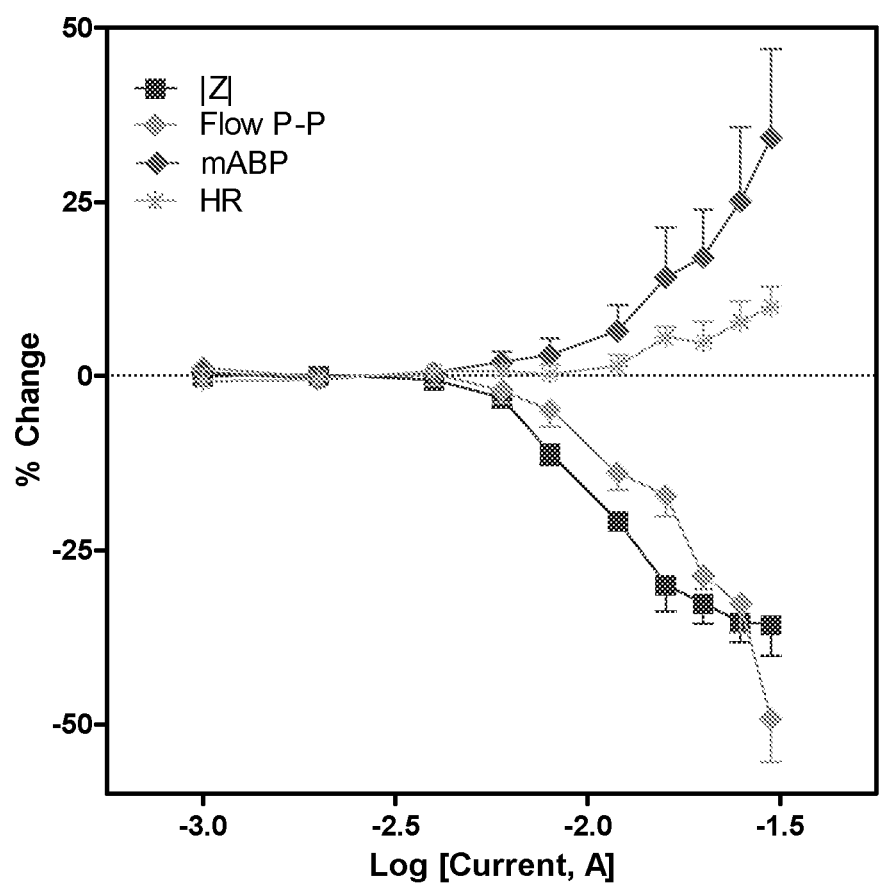
FIG. 3C illustrates a graph showing the effect of porcine splenic plexus stimulation on subthreshold impedance, |Z| (circles), splenic arterial flow (squares), mean arterial blood pressure (diamonds) and heart rate (asterisk) following 0.4 ms biphasic stimulation at 10 Hz for 1 min.

FIG. 3C illustrates a graph showing the effect of porcine splenic plexus stimulation on impedance (|Z|), splenic arterial flow, mean arterial blood pressure and heart rate. Impedance was calculated from the voltage envelope of a subthreshold (0.5-2 mA at 500 Hz, for example) sinusoidal carrier wave delivered continuously across the stimulating electrodes concomitant with the suprathreshold stimulation. Change in impedance was calculated in reference to the baseline resistance prior to the 1 mA stimulation.

Thus, FIGS. 3B and 3C illustrate that the impedance change measurement (likely a result of vascular contraction) provides dose response feedback and is strongly correlative to other biomarkers of splenic nerve activation including reduction in blood flow and increase in mean arterial blood pressure, heart rate, and eCAP within the splenic nerve.

The data for FIGS. 3B and 3C were obtained according to the following materials and methods:

Animals were sedated with ketamine and midazolam administered by intramuscular injection. An intravenous catheter was placed in one auricular vein, and anaesthesia was induced by propofol administered intravenously.

The surgical approach to SpN cuff implantation includes the following steps: The spleen was exteriorized and the splenic artery (SpA) was identified along its visceral surface. At the mid portion of the spleen, proximal to the SpA branching into the left gastroepiploic artery, a short segment of the SpA was carefully dissected free of surrounding soft tissue for placement of a 2 mm ultrasonic flow probe. After probe placement, the spleen was repositioned into the abdomen. The cuff was placed around the SpA and the intact peri-arterial SpN network. The tension on the spleen and artery was then released. SpA and SpV (splenic vein) blood flow readings were tested.

Electrophysiological experiments were also carried out. These generally entailed dissecting and cuffing (using a 500-600 µm diameter bipolar or tripolar CorTec cuff) one or several discrete SpN fascicles few centimetres distal (closer to the spleen) to the stimulating cuff to enable evoked compound action potential (eCAP) recording during stimulation of the whole SpN plexus or of few fascicles. Also, different combinations of blocking neural signalling (e.g. using topical administration of local anaesthesia, or transection of the SpN fascicle) either upstream or downstream of the stimulation site were performed.

Recorded eCAP were amplified and filtered (10-1000 Hz) using an 1800 2-Channel Microelectrode AC Amplifier (A-M system). Nerve activity was monitored continuously using an oscilloscope and recorded to a computer using a sampling rate of 15-20 kHz. eCAP were generally averaged (8 pulses) and peak to peak or area under the curve (AUC) of the averaged response quantified. The conduction velocity of the eCAP components of the SpN were calculated from the distance between stimulation and recording site and the latency of the eCAP signal.

Electrocardiogram (ECG), Heart rate (HR), arterial blood pressure, respiratory rate (RR), pulse oximetry, capnography, spirometry, and splenic artery blood flow were monitored throughout the surgery. Body temperature was recorded continuously with an intranasal probe. Arterial blood gasses were analysed throughout the experiment to monitor pH, Glucose, pO2 and pCO2, K+ levels. All physiological parameters as well as the level of used sevoflurane were recorded (every 5-10 minutes) on the record sheet. Physiological data were also digitalized. All parameters were generally sampled at a frequency between 0.1 and 2 kHz.

Constant current stimulation was delivered via a DS5 isolated bipolar current stimulator (Digitimer) driven by the Powerlab voltage output channels. Symmetrical bipolar square pulses of 0.4 msec were delivered at 10 Hz for 1 min.

Voltage across the output neural implant was digitized using a sampling rate of 250 kHz. Current delivered by the DS5 was digitized using a sampling rate of 10-20 kHz. The electrode-tissue interface access resistance was extracted from the voltage trace at the rising (or leading) edge of the stimulation pulse and change from baseline monitored for each stimulation current. In some instances, a 0.5-2 mA subthreshold constant current sinusoidal (500 Hz) carrier waveform was delivered continuously across the stimulating electrodes prior to, during, and post supramaximal square wave stimulation at 10 Hz as described above. The carrier wave was generated with an Analog Discovery 2 (Digilent) and converted to current with a Model 2200 Analog Stimulus Isolator (AM Systems). The voltage envelope of the subthreshold carrier wave was digitized and change from baseline monitored for each stimulation current. Voltage, current, and envelope voltage were digitized.

In this embodiment, current is injected between the stimulation electrodes during stimulation of the nerve. This stimulation may be provided by a voltage or current source 60 operatively connected to each of stimulation electrodes of each neural interface device. The voltage or current source is configured to generate an electrical signal to be applied to the nerve via the stimulation electrodes. In addition, the system comprises an impedance measurement module 70 operatively connected to each pair of impedance measuring electrodes. The impedance measurement module 70 is configured to measure the impedance between the pair of impedance measuring electrodes 13, 14. The system further comprises a controller 80 which is configured to receive the impedance measurements from the impedance measurement module 70 and to control the stimulation signal provided by the voltage or current source 60 based on the impedance measurements.

The impedance measurement current may be an AC current that is below an actuation threshold of the nerve (i.e. subthreshold stimulations, comprising the amplitude at which actuation is induced in the nerve). Also, the stimulation current may be at a different frequency than current that is injected between the impedance measurement electrodes. Most of the stimulation artefact appears as common mode signal across the impedance measurement electrodes and can be rejected by the impedance measurement circuit. Blanking (e.g. by using a blanking circuit) may also be utilised to minimised or block stimulation artefact.

Figure 2A:
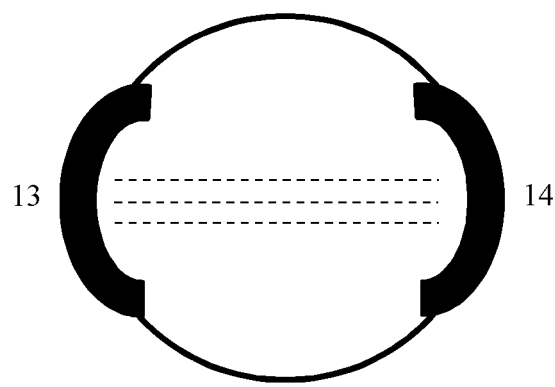
FIG. 2A illustrates a cross-section of the neural interface device mounted on a blood vessel in a non-contracted state.
Figure 2B:
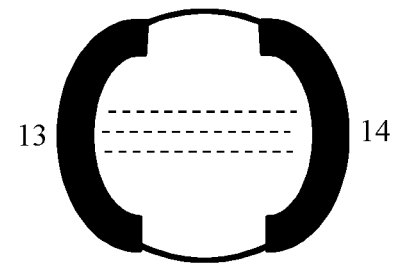
FIG. 2B illustrates a cross-section of the neural interface device mounted on a blood vessel in a non-contracted state.

The stimulation leads the blood vessel (e.g. splenic artery) to transition from a non-contracted state, which is illustrated in FIG. 2A, to a contracted stated, which is illustrated in FIG. 2B, via vasculature contraction. This causes the rate of blood flow in the blood vessel to change. In addition, this contraction changes the current path between the impedance measurement electrodes and leads to a reduction in impedance. The level of impedance reduction can be correlated with the amount of stimulation induced into the splenic artery, for instance via a look up table or through an established transfer function. In this way it is possible to determine the dose of stimulation applied to the nerve. It is therefore possible to adjust the stimulation provided in order to reach a particular target dose.

Referring to FIG. 4, the voltage or current source 60 provides stimulation to the nerve while the impedance measuring module 70 measures the impedance between the pair of electrodes 13, 14. The voltage or current source 60 is controlled in order to provide a stimulation signal that correspond with a particular target dose. For instance, the signal may have a particular amplitude, duration or pattern in order to provide the target dose. The impedance measuring module 70 measures the impedance and outputs the value of impedance to the controller 80. As explained above, the value of impedance is correlated with blood flow in order to determine the actual level of action potential being induced in the nerve. Thus, the controller 80 can be configured to determine if the target action potential, or target dose, is met by the stimulation being provided by the voltage or current source 60. If the target is met, the controller 80 maintains the level of stimulation provided. However, if the target is not met, the controller can increase or decrease the level of stimulation as appropriate in order for the target to be met.

This may be an iterative process which makes use of the feedback loop provided by the controller 80, voltage/current source 60 and the impedance measuring module.

Figure 5:
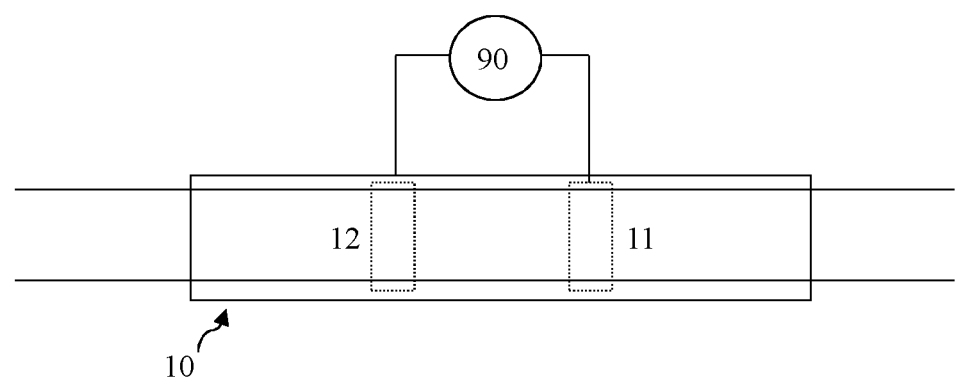
FIG. 5 illustrates another neural stimulation and impedance measuring system.

In another embodiment shown in FIG. 5, the neural interface device 10 does not use the impedance measuring electrode 13, 14, or the neural interface device is provided without these electrodes 13, 14. In this embodiment, impedance measurement is performed using the stimulation electrodes 11, 12 and the stimulation current is provided by a voltage/current source 90. This is an example embodiment in which a single pair of electrodes functions as both the stimulation electrodes and the impedance measurement electrodes. In some embodiments, the body of the subject (or body of the implant, CAN) serves as an electrode. In other words, a monopolar stimulation between either one of two electrodes 11 or 12 and the CAN may be provided, where impedance is sensed across the two internal electrodes 11 and 12. In another embodiment, the body of the subject (or body of the implant, CAN) serves as an electrode to enable monopolar stimulation between either one of two electrodes 11 or 12 and the CAN may be provided, where impedance is sensed across the remaining unused electrode 11 or 12 and the CAN.

In this embodiment, the ratio of the compliance voltage to the stimulation current changes during stimulation. The compliance voltage is defined as the voltage required to provide the desired current for a given load impedance, where load is the combination of the biology and electrode impedances. The level of the compliance voltage is indicative of the impedance of the electrodes 11, 12 plus the impedance of the artery. Due to the contraction of the artery during stimulation, the impedance will change along the artery due to the reduced cross section of the current path. This can be correlated with the amount of the stimulation current. The ratio of the compliance voltage to subthreshold stimulations also changes during subthreshold stimulation. Thus, the ratio of the compliance voltage to the subthreshold stimulation (AC current or pulse) can also be used as an indication of the impedance of the electrodes 11, 12 plus the impedance of the artery.

In this embodiment, the voltage/current source 90 can provide stimulation, measure impedance and adjust the stimulation signal based on the measured impedance. This can occur in a similar manner as explained above with reference to the voltage/current source 60, impedance measuring module 70 and controller 80.

The electrical signal applied to the nerve in the system described above is ideally non-destructive. As used herein, a "non-destructive signal" is a signal that, when applied, does not irreversibly damage the underlying neural signal conduction ability of the nerve. That is, application of a non-destructive signal maintains the ability of the nerve or fibres thereof, or other nerve tissue to which the signal is applied, to conduct action potentials when application of the signal ceases, even if that conduction is in practice artificially stimulated as a result of application of the non-destructive signal.

Stimulation of the neural activity of the nerve can be achieved using electrical signals which serve to replicate the normal neural activity of the nerve (i.e. the action potentials). Accordingly, the electrical signal may be a pulse train, the pulse train comprising a plurality of pulses (e,g, stimulation pulse may have a frequency of 1-10 Hz and an amplitude of 1-30 mA, 1-16 mA, these ranges may differ depending on the sensitivity of the system). The number of pulses per second in the pulse train is set by the frequency, and the duration of the pulses within each phase is determined by the pulse width. Thus, a pulse width refers to a width (or time duration) of a primary phase of the waveform. In cases where a pulse comprises a first phase that is the primary phase and a second phase which is the recovery phase, for example an anodic and/or a cathodic phase, the pulse width refers to a width (or duration) of the first phase.

The pulses may have a square, sawtooth, sinusoidal, triangular, trapezoidal, or quasitrapezodial waveform, though a square waveform is preferred for stimulation pulse. Other complex waveforms which are similar to the waveform of an action potential are also suitable with the disclosure.

The pulses may be biphasic pulses. The term "biphasic" refers to an electrical signal which causes each of the electrodes in the electrode arrangement 15 to be both positively and negatively charged over time. Biphasic pulses may be charge-balanced. The term "charge-balanced" in relation to a pulse train is taken to mean that the positive charge and negative charge applied by the signal over the pulse duration is equal.

Each pulse may have a pulse width of between 0.05 ms and 2.0 ms, and the current of the signal provided may be between 100 μA-50 mA, for example 10 mA, 30 mA. A subthreshold stimulation may have a current<2 mA. In particular, the pulses may have a pulse width of at least one of: 0.1 ms, 0.2 ms, 0.4 ms, 0.6 ms, 0.8 ms, 1 ms, 1.2 ms, 1,4 ms, 1.6 ms, 1.8 ms and 2 ms.

Figure 8:
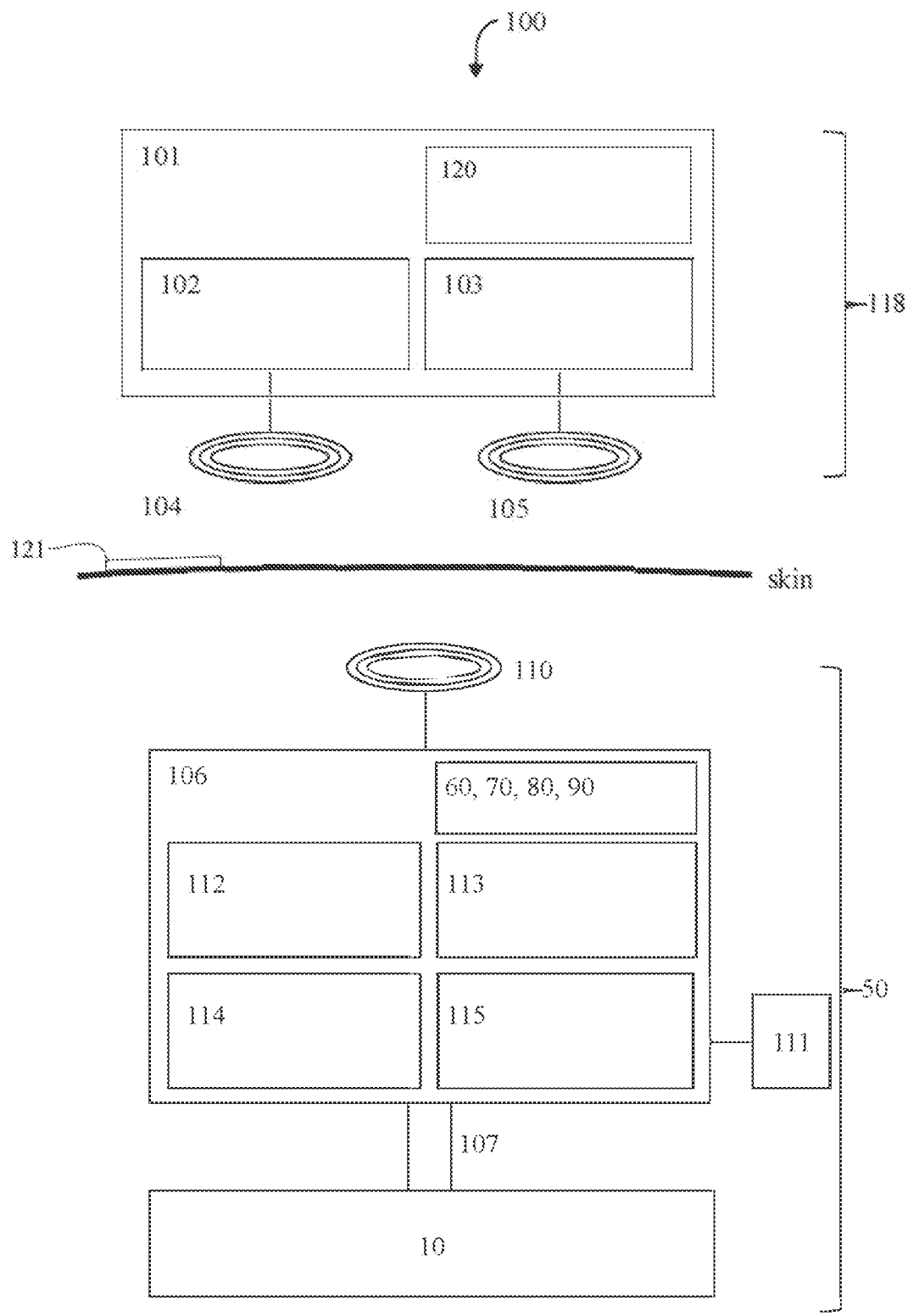
FIG. 8 illustrates a wider system including the neural stimulation system.

Referring to FIG. 8, the neural interface device 10 and voltage or current source 60, the neural stimulation system 50 may comprise one or more of the following components: a microprocessor 113; an implantable transceiver 110; a physiological sensor 111; a power source 112; a memory 114 (otherwise referred to as a non-transitory computer-readable storage device); and a physiological data processing module 115.

One or more of the following components may be contained within an implantable device 106: the voltage or current source 60 90, the impedance measuring module 70, the controller 80, the power source 112; the memory 114; the microprocessor 113, and the physiological data processing module 115.

The microprocessor 113 may be responsible for triggering the beginning and/or end of the electrical signals to be applied to the nerve. Optionally, microprocessor 113 may also be responsible for generating and/or controlling the signal parameters, including the pulse width.

The microprocessor 113 may be configured to operate in an open-loop fashion, wherein a pre-defined signal (e.g. as described above) is applied to the nerve at a given periodicity (or continuously) and for a given duration (or indefinitely) with or without an external trigger, and without any control or feedback mechanism. Alternatively, the microprocessor 113 may be configured to operate in a closed-loop fashion, wherein an electrical signal is applied based on a control or feedback mechanism. As described elsewhere herein, the external trigger may be an external controller 101 operable by the operator to initiate application of an electrical signal.

The microprocessor 113 may be constructed so as to generate, in use, a preconfigured and/or operator-selectable signal that is independent of any input. Alternatively, the microprocessor 113 may be responsive to an external signal, for example information (e.g. data) pertaining to one or more physiological parameters of the subject in which the neural stimulation system 50 is implanted.

The microprocessor 113 may be triggered upon receipt of a signal generated by an operator, such as a physician or the subject in which the neural stimulation system 50 is implanted. To that end, the neural stimulation system 50 may be part of a wider system 100 which additionally comprises an external system 118 comprising a controller 101. An example of the wider system 100 is described below.

External system 118 of wider system 100 is external the neural stimulation system 50 and external to the subject, and comprises controller 101. Controller 101 may be used for controlling and/or externally powering neural stimulation system 50. To this end, controller 101 may comprise a powering unit 102 and/or a programming unit 103. The external system 118 may further comprise a power transmission antenna 104 and a data transmission antenna 105, as further described below.

The controller 101 and/or microprocessor 113 may be configured to apply the electrical signal to the nerve periodically or continuously. Periodic application of an electrical signal involves applying the signal in an (on-off)$_n$ pattern, where n>1. For instance, the electrical signal can be applied continuously for a duration of time, before ceasing for a period, before being again applied continuously for a second duration of time, etc.

The signal may be applied by controller 101 and/or microprocessor 113 for a specific amount of times per day. For instance, the signal may be applied in bursts across the day.

Continuous application may continue indefinitely, e.g. permanently. Alternatively, the continuous application may be for a minimum period, for example the signal may be continuously applied for at least 5 days, or at least 7 days.

Whether the signal applied to the nerve is controlled by controller 101, or whether the signal is continuously applied directly by microprocessor 113, although the signal might be a series of pulses, the gaps between those pulses do not mean the signal is not continuously applied.

The signal may be applied only when the subject is in a specific state e.g. only when the subject is awake, only when the subject is asleep, prior to and/or after the ingestion of food, prior to and/or after the subject undertakes exercise, etc.

Timing for stimulation of neural activity in the nerve may be achieved using controller 101.

The power source 112 may comprise a current source and/or a voltage source for providing power to the current or voltage source 50. The power source 112 may also provide power for the other components of the implantable device 106 and/or neural stimulation system 50, such as the microprocessor 113, memory 114, and implantable transceiver 110. The power source 112 may comprise a battery, the battery may be rechargeable.

It will be appreciated that the availability of power is limited in implantable devices, and the invention has been devised with this constraint in mind. The implantable device 106 and/or neural stimulation system 50 may be powered by inductive powering or a rechargeable power source.

Memory 114 may store power data and data pertaining to the one or more physiological parameters from internal neural stimulation system 50. For instance, memory 114 may store data pertaining to one or more signals indicative of the one or more physiological parameters detected by physiological sensor 111, and/or the one or more corresponding physiological parameters determined via physiological data processing module 115. In addition or alternatively, memory 114 may store power data and data pertaining to the one or more physiological parameters from external system 118 via the implantable transceiver 110. To this end, the implantable transceiver 110 may form part of a communication subsystem of the wider system 100, as is further discussed below.

The physiological data processing module 115 is configured to process one or more signals indicative of one or more physiological parameters in a subject detected by the physiological sensor 111, to determine one or more corresponding physiological parameters. Physiological data processing module 115 may be configured for reducing the size of the data pertaining to the one or more physiological parameters for storing in memory 114 and/or for transmitting to the external system via implantable transceiver 110. Implantable transceiver 110 may comprise an one or more antenna(e). The implantable transceiver 100 may use any suitable signalling process such as RF, wireless, infrared and so on, for transmitting signals outside of the body, for instance to wider system 100 of which the neural stimulation system 50 is one part.

Alternatively or additionally, physiological data processing module 115 may be configured to process the signals indicative of the one or more physiological parameters and/or process the determined one or more physiological parameters to determine the evolution of the disease in the subject. In such case, the neural stimulation system 50, in particular the implantable device 106, will include a capability of calibrating and tuning the signal parameters based on the one or more physiological parameters of the subject and the determined evolution of the disease in the subject.

The physiological data processing module 115 and the at least one physiological sensor 111 may form a physiological sensor subsystem, also known herein as a detector, either as part of the neural stimulation system 50, part of the implantable device 106, or external to the system.

Physiological sensor 111 comprises one or more sensors, each configured to detect a signal indicative of one of the one or more physiological parameters described above. For example, the physiological sensor 110 is configured for: detecting biomolecule concentration using electrical, RF or optical (visible, infrared) biochemical sensors; detecting blood flow using intra- or perivascular flow tubes in or around an artery; detecting neural activity of a nerve using an electrical sensor; or a combination thereof.

The physiological parameters determined by the physiological data processing module 115 may be used to trigger the microprocessor 113 to apply an electrical signal to the nerve via the electrode arrangement 15. Upon receipt of the signal indicative of a physiological parameter received from physiological sensor 111, the physiological data processor 115 may determine the physiological parameter of the subject, and the evolution of the disease, by calculating in accordance with techniques known in the art.

The memory 114 may store physiological data pertaining to normal levels of the one or more physiological parameters. The data may be specific to the subject into which the neural stimulation system 50 is implanted, and gleaned from various tests known in the art. Upon receipt of the signal indicative of a physiological parameter received from physiological sensor 111, or else periodically or upon demand from physiological sensor 111, the physiological data processor 115 may compare the physiological parameter determined from the signal received from physiological sensor 111 with the data pertaining to a normal level of the physiological parameter stored in the memory 114, and determine whether the received signals are indicative of insufficient or excessive of a particular physiological parameter, and thus indicative of the evolution of the disease in the subject.

The neural stimulation system 50 may be configured such that if and when an insufficient or excessive level of a physiological parameter is determined by physiological data processor 115, the physiological data processor 115 triggers application of the electrical signal to the nerve via the electrode arrangement 15, in the manner described elsewhere herein. For instance, if physiological parameter indicative of worsening of any of the physiological parameters and/or of the disease is determined, the physiological data processor 115 may trigger application of an electrical signal which dampens secretion of the respective biochemical, as described elsewhere herein. Particular physiological parameters relevant to the present invention are described above. When one or more signals indicative of one or more of these physiological parameters are received by the physiological data processor 115, an electrical signal may be applied to the nerve via the electrode arrangement 15.

Controller 101 may be configured to make adjustments to the operation of the neural stimulation system 50. The data may be specific to the patient into which the device is implanted. The controller 101 may also be configured to make adjustments to the operation of the power source 112, signal generator 60 and processing elements 113, 115 and/or neural interfacing element 10 in order to tune the electrical signal applied to the nerve via the electrode arrangement 15.

Figure 6:
FIG. 6 is an illustration of wave form used to stimulate and assess dose response via impedance measurement after injection of subthreshold current (sinusoidal carrier wave)
Figure 7:
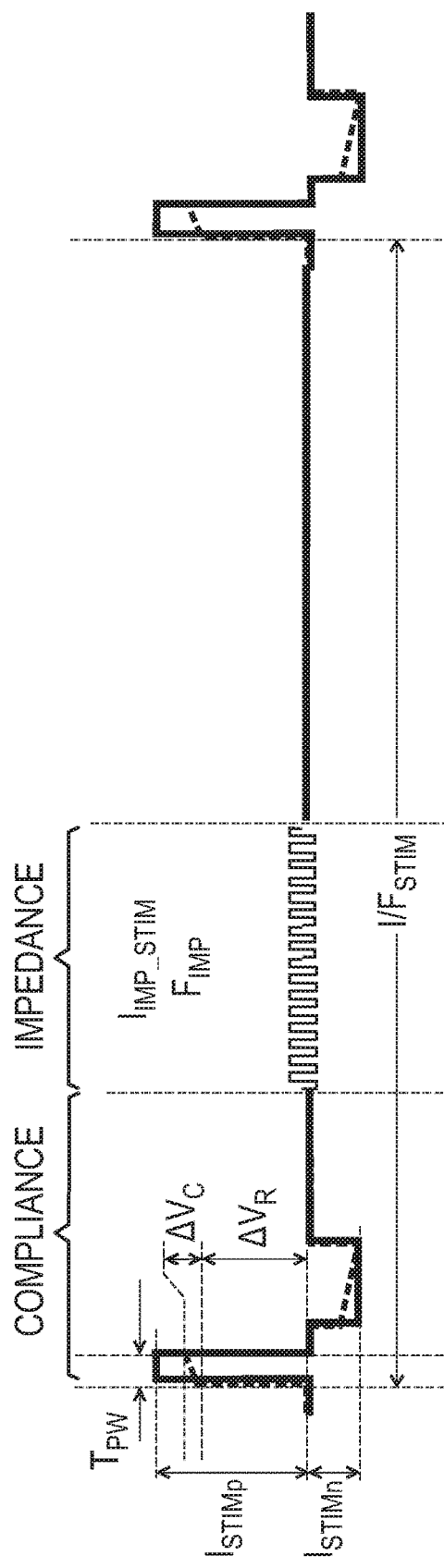
FIG. 7 is another illustration of wave form used to stimulate and assess does response via impedance measurement after injection of subthreshold current (pulse)

FIGS. 6 and 7 illustrate waveform to achieve stimulation simultaneous to dose response via impedance measurements, particularly where a subthreshold current is injected in between stimulation pulses. In FIG. 6, the subthreshold waveform is a sinusoidal wave. In FIG. 7, the subthreshold waveform is square wave pulses. As previously noted, subthreshold stimulation waveform refers to those waveforms having an amplitude that is lower than a threshold, the threshold being the amplitude which induces a nerve activation. Impedance can also be extracted from the access resistance of the stimulation pulse $\Delta V_R$.

In both FIGS. 6 and 7, the injected current waveform (lighter colour in grayscale) and the resultant voltage waveform (darker colour in grayscale) are illustrated in an overlapped manner. Of the overlapped waveforms, the asymmetric square pulse wave having $I_{STIMp}$ and $I_{STIMn}$ is the stimulation pulse, and the resulting voltage waveform having $\Delta V_C$ (which indicates polarization capacitance) and $\Delta V_R$ (which indicates access resistance) represents the impedance change seen across the stimulating electrodes. The impedance change caused by the electrical dose may be measured by extracting the real-time change in access resistance and/or polarization capacitance directly from compliance voltages across stimulating electrodes during the stimulation pulse. As illustrated, the impedance change caused by an applied electrical dose may also be measured by detecting the impedance of a subthreshold signal injected between the stimulation pulses across stimulating electrodes.

More specifically, where the subthreshold current is injected an impedance response, similar to those seen for the stimulation current and impedance response, occurs. That is to say, in response to the subthreshold pulse portion an impedance response occurs as illustrated by the overlapping subthreshold pulses in FIGS. 6 and 7.

Thus, a number of different methods of measuring (or evaluating) impedance have been discussed above. In one method, the impedance is evaluated by voltage build-up at the electrode during the initial rising phase $\Delta V_R$ of stimulation period (TPW) and dividing it with the current amplitude ($I_{STIMp}$). In another method, impedance is measured by injecting a subthreshold current in between stimulation pulses, where the impedance is evaluated by measuring voltage (rising phase, peak, envelope, phase) generated over the electrodes and dividing it by subthreshold current amplitude. The subthreshold waveforms could be sinusoidal waves or could be square wave pulses at an amplitude that is lower than to induce nerve activation. In yet another method, impedance is measured by simply measuring the polarization capacitance ($\Delta V_C$) or the access resistance ($\Delta V_R$) of the impedance change induced by a stimulation pulse and/or a subthreshold stimulation.

Measuring impedance using the subthreshold signal as described in above various embodiments enables impedance measurement regardless of stimulation status without evoking any physiological response in a subject. In other words, using a subthreshold signal enables a dose response monitoring without evoking any physiological response in a subject. Thus, a constant and/or an uninterrupted impedance measurement or dose response monitoring can be carried out.

In some embodiments, a subthreshold signal and/or stimulation signal may be injected by using electrodes 12 and 11, and the same electrodes 12 and 11 may be used to measure impedance using any of the methods discussed above. In other embodiments, a subthreshold signal and/or stimulation signal may be inserted using electrodes 12 and 11, and different electrodes 13 and 14 may be used to measure impedance using any of the methods discussed above. When measuring electrodes differ from stimulating electrodes, it is possible to reduce and/or exclude any impact of current injection, thus obtaining a more accurate measurement at the measuring electrodes.

Wider System

With reference to FIG. 8, the neural stimulation device may be part of a wider system 100 that includes a number of subsystems, for example the external system 118. The external system 118 may be used for powering and programming the neural stimulation system 50 through human skin and underlying tissues.

The external subsystem 118 may comprise, in addition to controller 101, one or more of: a powering unit 102, for wirelessly recharging the battery of power source 112 used to power the implantable device 106; and a programming unit 103 configured to communicate with the implantable transceiver 110. The programming unit 103 and the implantable transceiver 110 may form a communication subsystem. The powering unit 102 may be housed together with programing unit 103; alternatively, they can be housed in separate devices.

The external subsystem 118 may also comprise one or more of: power transmission antenna 104; and data transmission antenna 105. Power transmission antenna 104 may be configured for transmitting an electromagnetic field at a low frequency (e.g., from 30 kHz to 10 MHz). Data transmission antenna 105 may be configured to transmit data for programming or reprogramming the implantable device 106, and may be used in addition to the power transmission antenna 104 for transmitting an electromagnetic field at a high frequency (e.g., from 1 MHz to 10 GHz). The temperature in the skin will not increase by more than 2 degrees Celsius above the surrounding tissue during the operation of the power transmission antenna 104. The at least one antennae of the implantable transceiver 110 may be configured to receive power from the external electromagnetic field generated by power transmission antenna 104, which may be used to charge the rechargeable battery of power source 112.

The power transmission antenna 104, data transmission antenna 105, and the at least one antennae of implantable transceiver 110 have certain characteristics such a resonant frequency and a quality factor (Q). One implementation of the antenna(e) is a coil of wire with or without a ferrite core forming an inductor with a defined inductance. This inductor may be coupled with a resonating capacitor and a resistive loss to form the resonant circuit. The frequency is set to match that of the electromagnetic field generated by the power transmission antenna 105. A second antenna of the at least one antennae of implantable transceiver 110 can be used in neural stimulation system 50 for data reception and transmission from/to the external system 118. If more than one antenna is used in the neural stimulation system 50, these antennae are rotated 30 degrees from one another to achieve a better degree of power transfer efficiency during slight misalignment with the power transmission antenna 104.

External system 118 may comprise one or more external body-worn physiological sensors 121 (not shown) to detect signals indicative of one or more physiological parameters. The signals may be transmitted to the neural stimulation system 50 via the at least one antennae of implantable transceiver 110. Alternatively or additionally, the signals may be transmitted to the external neural stimulation system 50 and then to the neural stimulation system 50 via the at least one antennae of implantable transceiver 110. As with signals indicative of one or more physiological parameters detected by the implanted physiological sensor 111, the signals indicative of one or more physiological parameters detected by the external sensor 121 may be processed by the physiological data processing module 115 to determine the one or more physiological parameters and/or stored in memory 114 to operate the neural stimulation system 50 in a closed-loop fashion. The physiological parameters of the subject determined via signals received from the external sensor 121 may be used in addition to alternatively to the physiological parameters determined via signals received from the implanted physiological sensor 111.

The wider system 100 may include a safety protection feature that discontinues the electrical stimulation of the nerve in the following exemplary events: abnormal operation of the neural stimulation system 50 (e.g. overvoltage); abnormal readout from an implanted physiological sensor 111 (e.g. temperature increase of more than 2 degrees Celsius or excessively high or low electrical impedance at the electrode-tissue interface); abnormal readout from an external body-worn physiological sensor 121 (not shown); or abnormal response to stimulation detected by an operator (e.g. a physician or the subject). The safety precaution feature may be implemented via controller 101 and communicated to the neural stimulation system 50, or internally within the neural stimulation system 50.

The external system 118 may comprise an actuator 120 (not shown) which, upon being pressed by an operator (e.g. a physician or the subject), will apply the electrical signal, via controller 101 and the respective communication subsystem, to trigger the microprocessor 113 of the neural stimulation system 50 to apply the electrical signal to the nerve by the electrode arrangement 15.

Wider system 100 of the invention, in particular neural stimulation system 50, is preferably made from, or coated with, a biostable and biocompatible material. This means that the system is both protected from damage due to exposure to the body's tissues and also minimises the risk that the system elicits an unfavorable reaction by the host (which could ultimately lead to rejection). The material used to make or coat the system should ideally resist the formation of biofilms. Suitable materials include, but are not limited to, poly(p-xylylene) polymers (known as Parylenes) and polytetrafluoroethylene.

General

The methods described herein may be performed by software in machine readable form on a tangible storage medium e.g. in the form of a computer program comprising computer program code means adapted to perform all the steps of any of the methods described herein when the program is run on a computer and where the computer program may be embodied on a computer readable medium. Examples of tangible (or non-transitory) storage media include disks, thumb drives, memory cards etc. and do not include propagated signals. The software can be suitable for execution on a parallel processor or a serial processor such that the method steps may be carried out in any suitable order, or simultaneously. This acknowledges that firmware and software can be valuable, separately tradable commodities. It is intended to encompass software, which runs on or controls "dumb" or standard hardware, to carry out the desired functions. It is also intended to encompass software which "describes" or defines the configuration of hardware, such as HDL (hardware description language) software, as is used for designing silicon chips, or for configuring universal programmable chips, to carry out desired functions.

Those skilled in the art will realise that storage devices utilised to store program instructions can be distributed across a network. For example, a remote computer may store an example of the process described as software. A local or terminal computer may access the remote computer and download a part or all of the software to run the program. Alternatively, the local computer may download pieces of the software as needed, or execute some software instructions at the local terminal and some at the remote computer (or computer network). Those skilled in the art will also realise that by utilising conventional techniques known to those skilled in the art that all, or a portion of the software instructions may be carried out by a dedicated circuit, such as a DSP, programmable logic array, or the like.

Unless otherwise indicated each embodiment as described herein may be combined with another embodiment as described herein. The term "comprising" encompasses "including" as well as "consisting" e.g. a composition "comprising" X may consist exclusively of X or may include something additional e.g. X+Y.

It will be understood that the benefits and advantages described above may relate to one embodiment or may relate to several embodiments. The embodiments are not limited to those that solve any or all of the stated problems or those that have any or all of the stated benefits and advantages.

It will be understood that the above description of a preferred embodiment is given by way of example only and that various modifications may be made by those skilled in the art. Although various embodiments have been described above with a certain degree of particularity, or with reference to one or more individual embodiments, those skilled in the art could make numerous alterations to the disclosed embodiments without departing from the scope of this invention.

The invention claimed is:

1. A system for stimulation of a nerve and measuring impedance, the system comprising:
    a plurality of electrodes;
    a voltage or current source operatively connected to at least a subset of the plurality of electrodes, wherein the voltage or current source is configured to generate an electrical signal to be applied to said subset of the plurality of electrodes;
    an impedance measurement module operatively connected to at least the subset of the plurality of electrodes, wherein the impedance measurement module is configured to measure the impedance between said subset of the plurality of electrodes,
    wherein the impedance measurement module is further configured to measure a relative change in impedance between a baseline impedance measured before an application of the electrical signal and an impedance measured after the application of the electrical signal comprising a sequence of stimulation pulses, across the plurality of electrodes; and
    a controller arranged to determine a dose response induced by the electrical signal,
    wherein the dose response is determined using relationship definitions based upon correlation data between impedance change and the dose response,
    wherein the dose response is an indication of a downstream effect, and
    wherein the controller is arranged to adjust the electrical signal in order to induce a target dose response.

2. The system of claim 1, wherein the voltage or current source is operatively connected to a pair of stimulation electrodes.

3. The system of claim 2, wherein the pair of stimulation electrodes are configured to provide stimulation to the nerve and to measure the impedance between said subset of electrodes.

4. The system of claim 2, wherein the voltage or current source is configured to apply the electrical signal to the pair of stimulation electrodes, such that a first electrode of the pair of stimulation electrodes becomes positively charged and a second electrode of the pair of stimulation electrodes becomes negatively charged.

5. The system of claim 2, wherein the impedance measurement module is configured to measure the impedance between said subset of the electrodes by measuring a differential voltage induced across the pair of stimulation electrodes.

6. The system of claim 5, wherein the impedance measurement module is configured to extract a voltage at the rising edge of at least one of the stimulation pulses to determine an indication of an access resistance.

7. The system of claim 5, wherein the impedance measurement module is configured to extract a difference between the peak electrode voltage at a falling edge and the rising edge of at least one of the stimulation pulses to determine an indication of a polarization capacitance.

8. The system of claim 2, wherein the impedance measurement module is configured to measure a differential voltage across the pair of stimulation electrodes while applying a subthreshold sequence of pulses in between two successive pulses of a stimulating pulse.

9. The system of claim 1, wherein the impedance measurement module is operatively connected to a pair of impedance measurement electrodes.

10. The system of claim 1, wherein the electrical signal comprises a pulse train, the pulse train comprising a plurality of pulses.

11. The system of claim 10, wherein the plurality of pulses have a waveform which is a square, sawtooth, sinusoidal, triangular, trapezoidal, quasitrapezodial or complex waveform.

12. A method for stimulation of a nerve and measuring the impedance, the method comprising:
providing a system according to claim 1, wherein the plurality of electrodes comprise stimulation electrodes and impedance measurement electrodes;
generating the electrical signal to be applied to the nerve via the stimulation electrodes by at least one voltage or current source operatively connected to the stimulation electrodes; and
measuring the impedance between the impedance measurement electrodes by at least one impedance measurement module operatively connected to the impedance measurement electrodes.

13. The method of claim 12, further comprising:
determining an amplitude of an action potential induced in the nerve based on the measured impedance; and
adjusting the electrical signal in order to induce an action potential having a target amplitude.

14. The system of claim 2, wherein the impedance measurement module is configured to measure compliance voltage across the pair of stimulation electrodes during a stimulation pulse.

15. The system of claim 1, wherein one of the plurality of electrodes is provided as at least a part of a body of an implant comprising the voltage or current source.

16. The system of claim 1, wherein at least a portion of the controller is implanted in a patient.

17. The system of claim 1, wherein at least a portion of the controller is external.

18. A system for stimulation of a nerve and measuring impedance, the system comprising:
one or more neural interface devices comprising:
a pair of stimulation electrodes for inducing an electrical signal in the nerve; and
a pair of impedance measurement electrodes for measuring impedance between the impedance measurement electrodes, wherein the pair of stimulation electrodes are spaced apart from one another in a longitudinal direction with respect to the nerve, and wherein the pair of impedance measurement electrodes are spaced apart from one another in a direction perpendicular to the longitudinal direction with respect to the nerve;
a voltage or current source operatively connected to each pair of stimulation electrodes of each of the one or more neural interface devices, wherein the voltage or current source is configured to generate the electrical signal to be applied to the nerve via the stimulation electrodes; and
an impedance measurement module operatively connected to each pair of impedance measurement electrodes, wherein the impedance measurement module is configured to measure a relative change in impedance between a baseline impedance measured before an application of the electrical signal and an impedance measured after the application of the electrical signal comprising a sequence of stimulation pulses, across the pair of impedance measurement electrodes; and
a controller arranged to determine a dose response induced by the electrical signal,
wherein the dose response is determined using relationship definitions based upon correlation data between impedance change and the dose response,
wherein the dose response is an indication of a downstream effect, and
wherein the controller is arranged to adjust the electrical signal in order to induce a target dose response.

19. The system of claim 18, further comprising at least one cuff portion having an assembled position in which the cuff portion forms at least part of a passageway for receiving the nerve in the longitudinal direction of the nerve.

20. The system of claim 18, wherein the pair of stimulation electrodes comprises a first conductive ring and a second conductive ring.

21. The system of claim 18, wherein the pair of impedance measurement electrodes comprises a first conductive element and a second conductive element, wherein the first conductive element is diametrically opposed to the second conductive element.

22. The system of claim 18, wherein each one of the impedance measurement electrodes is positioned between the pair of stimulation electrodes.

23. The system of claim 18, wherein the controller is configured to determine an amplitude of an action potential induced in the nerve, via the electrical signal, based on the measured impedance and to adjust the electrical signal.

24. The system of claim 18, wherein one of the pair of stimulation electrodes is provided as at least a part of a body of an implant comprising the voltage or current source.

* * * * *